United States Patent [19]

Morgan et al.

[11] Patent Number: 4,918,228

[45] Date of Patent: Apr. 17, 1990

[54] QUATERNARY AMMONIUM ACRYLIC MONOMERS AND ALCOHOL SOLUBLE POLYMERS MADE THEREFROM

[75] Inventors: Michael E. Morgan; Martha A. Phelps, both of Louisville, Ky.

[73] Assignee: Hi-Tek Polymers, Inc., Jeffersontown, Ky.

[21] Appl. No.: 313,908

[22] Filed: Feb. 23, 1989

[51] Int. Cl.$^4$ ............................................. C07C 103/60
[52] U.S. Cl. .................................................... 564/208
[58] Field of Search .......................................... 564/208

[56] References Cited

U.S. PATENT DOCUMENTS 4,180,643 12/1979 Moss et al. ............................ 564/208

Primary Examiner—Joseph L. Schofer
Assistant Examiner—Alex H. Walker
Attorney, Agent, or Firm—Herbert P. Price

[57] ABSTRACT

Quaternary ammonium containing monomers, represented by the formula:

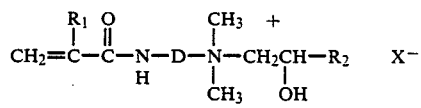

wherein $R_1$ is H or methyl, $R_2$ is an alkyl group containing 6 to 22 carbon atoms, D is an alkylene group containing 1 to 4 carbon atoms, or a hydroxyalkylene group containing 2 to 4 carbon atoms and X is an anion, are polymerized to form polymers useful in hair care preparations.

7 Claims, No Drawings 4,918,228

QUATERNARY AMMONIUM ACRYLIC MONOMERS AND ALCOHOL SOLUBLE POLYMERS MADE THEREFROM

BACKGROUND OF THE INVENTION

The field of art to which this invention is directed is quaternary ammonium acrylic monomers.

Acrylic monomers containing a quaternary ammonium group are well known and have been used to make polymers having particular use in hair care preparations. In U.S. Pat. No. 4,152,307, acrylate, methacrylate, acrylamide and methacrylamide monomers containing a quaternary ammonium group are described. Such monomers are represented by the structural formula:

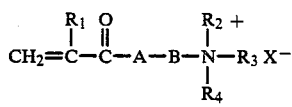

wherein $R_1$ is H or $CH_3$; $R_2$ and $R_3$ are independently an alkyl group having 1 to 4 Carbon atoms or a hydroxyalkyl group having 2 to 4 carbon atoms; $R_4$ is H, an alkyl group having 1 to 4 carbon atoms, a hydroxyalkyl group having 2 to 4 carbon atoms or a benzyl group; A is O or NH; B is an alkylene group or a hydroxyalkylene group and X is an anion. Similar monomers and polymers made therefrom are described in U.S. Pat. Nos. 4,075,183 and 4,419,344.

In U.S. Pat. No. 3,678,098, monomers such as dimethylaminoethyl methacrylate, are reacted with epichlorohydrin to form a quaternary ammonium group containing an alkylene chlorohydrin substituent.

U.S. Pat. Nos. 4,492,802 and 4,744,977 describe processes for the manufacture of quaternary ammonium compounds by reacting a compound containing a terminal epoxide group with a salt of a tertiary amine in the presence of a quaternary ammonium compound as catalyst.

Liquid detergent compositions, as described in U.S. Pat. No. 4,454,060, are made with copolymers of monomers such as those disclosed in U.S. Pat. No. 4,152,207 described hereinabove, and monomers which are long chain acrylates or methacrylates.

Hair dressing compositions, particularly those which are used to maintain hair in place, must be capable of being applied as a spray, must dry very fast to a non-tacky state, must be flexible and non-brittle and must be capable of being removed from the hair readily by washing and shampooing.

SUMMARY OF THE INVENTION

This invention is directed to quaternary ammonium group containing monomers and polymers made therefrom. In one aspect, this invention relates to quaternary ammonium group containing monomers wherein one of the alkyl substituents on the quaternary nitrogen is a long chain hydroxyalkyl group. In another aspect, this invention pertains to polymers made from the monomers. In still another aspect, this invention relates to hair grooming compositions made from the polymers.

The composition of this invention is a quaternary ammonium containing monomer represented by the structure

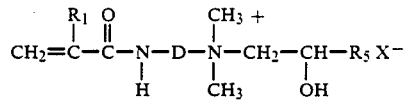

wherein $R_1$ is H or methyl; wherein $R_5$ is an alkyl group containing 6 to 22 carbon atoms, D is an alkylene group containing 1 to 4 carbon atoms or a hydroxyalkylene group containing 2 to 4 carbon atoms and X is an anion.

The monomers of this invention can be homopolymerized or copolymerized with other monomers to form polymers which are particularly useful in hair care formulations.

DESCRIPTION OF THE INVENTION

The monomers of this invention are prepared by reacting a long chain epoxy compound with a monomer containing a tertiary amine group, such a monomer being dimethylamino alkyl or hydroxyalkyl acrylamide or methacrylamide represented by the structure

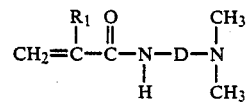

wherein $R_1$ is H or methyl and D is an alkylene group containing 1 to 4 carbon atoms or a hydroxyalkylene group containing 2 to 4 carbon atoms. Examples of such compounds are dimethylamino methyl acrylamide, dimethylaminoethyl methacrylamide, dimethylaminopropyl methacrylamide, dimethylamino-hydroxypropyl acrylamide, and the like.

The epoxy compounds which are reacted with the tertiary amine containing monomer are straight or branched chain 1,2-epoxyalkanes which contain 8 to 24 carbon atoms. These epoxy compounds can be represented by the structure:

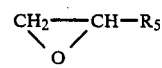

wherein $R_5$ is an alkyl group containing 6 to 22 carbon atoms, preferably 6 to 14 carbon atoms. Examples of useful epoxy compounds are 1,2-epoxyoctane, 1,2-epoxydecane, 1,2-epoxydodecane, 1,2-epoxyoctadecane and the like. Mixtures of two or more of these epoxy compounds can be used in this invention. Epoxy compounds wherein $R_5$ represents an alkyl group containing 1 to 5 carbon atoms can also be reacted with the tertiary amine containing monomer in admixture with the epoxy compounds wherein $R_5$ is an alkyl group containing 6 to 22 carbon atoms.

The anion, represented by $X^-$, can be derived from organic and inorganic acids, such as hydrochloric acid, sulfuric acid, phosphoric acid, hydrobromic acid, hydroiodic acid, acetic acid, propionic acid, formic acid and the like. A preferred acid is hydrochloric acid with the anion being a chloride ion.

In preparing the compositions of this invention, the tertiary amine containing monomer is dissolved in water or a water miscible alcohol, i.e., a 1 to 3 carbon alcohol namely methanol, ethanol, or isopropanol, or mixtures of water and the alcohol. The mixture will generally contain about 90 to about 10 parts by weight of water to about 10 to about 90 parts of alcohol. A preferred alcohol is ethanol. To the solution of tertiary amine containing monomer, the epoxy compound is added. The temperature during the addition is controlled at about 30° C. to about 75° C. After the addition of epoxy compound is completed, heating at about 30° C. to about 75° C. is continued to complete the reaction. The extent of reaction can be determined by the disappearance of epoxy groups. When the epoxy-tertiary amine quaternization reaction is completed, an acid is added to produce the quaternary ammonium salt.

In carrying out the reaction, the tertiary amine containing monomer and the epoxy compound are reacted in substantially molar equivalent amounts. The quaternary ammonium salt formation is also accomplished by substantial neutralization of the quaternary ammonium hydroxide with the acid.

The following examples describe the invention in more detail. Parts and percentages are by weight unless otherwise indicated.

EXAMPLE 1

To a suitable reactor equipped with a mechanical agitator, air sweep, addition funnel and a Claisen adapter with a thermometer and a reflux condenser were added 85.1 parts of dimethylaminopropyl methacrylamide, 42.7 parts of deionized water, and 74 parts of ethanol. The mixture was heated to 60° C. and slow addition was begun of 1,2-epoxyhexadecane from the dropping funnel. The addition of 120 parts of 1,2-epoxyhexadecane was completed in 60 minutes while keeping the temperature at 60° C. Heating at 60° C. was continued for 90 minutes to complete the reaction. The temperature was lowered to room temperature and 48.1 parts of 37 percent hydrochloric acid in water were slowly added with cooling to keep the temperature below 30° C. When the addition was complete, the solution was filtered to remove turbidity.

EXAMPLE 2

Using the same procedure described in Example 1, 127.7 parts of dimethylaminopropyl methacrylamide, in 60.4 parts of deionized water and 60.5 parts of ethanol, were reacted with 96.2 parts of 1,2-epoxyoctane, followed by neutralization with 74 parts of 37 percent hydrochloric acid.

EXAMPLE 3

Using the same procedure described in Example 1, 85.1 parts of dimethylaminopropyl methacrylamide, in 42.7 parts of deionized water and 74 parts of ethanol, were reacted with 92 parts of 1,2-epoxydodecane, followed by neutralization with 48.1 parts of 37 percent hydrochloric acid.

EXAMPLE 4

To a suitable reactor equipped as described in Example 1 were added 85.1 parts of dimethylaminopropyl methacrylamide and 80.1 parts of deionized water. Propylene oxide, 26.2 parts, and 1,2-epoxyoctane, 6.4 parts, were added to the dropping funnel. The mixture of epoxy compounds was slowly added at such a rate to keep the temperature at or below 50° C. When the addition was completed, the temperature was raised to 60° C. and was held at 60° C. for 90 minutes. The temperature was lowered to room temperature and 48.1 parts of 37 percent hydrochloric acid was added with cooling. The resulting solution was then filtered.

EXAMPLE 5

Using the same procedure described in Example 4, 127.7 parts of dimethylaminopropyl methacrylamide in 127 parts of deionized water were reacted with 43.6 parts of propylene oxide followed by neutralization with 74 parts of 37 percent hydrochloric acid.

The monomers of this invention are readily polymerized and the aqueous - alcoholic solutions resulting from the synthesis described in the foregoing examples can be employed directly for this purpose. Any known polymerization initiator of the free radical type can be used, examples of which are t-butyl peroxide, ammonium persulfate, alkali metal persulfates, the tetra sodium salt of ethylene diamine tetra acetic acid (EDTA), 2,2'-azobis(2-amidinopropane) hydrochloride, or mixtures thereof. The initiator is usually effective in quantities between about 0.01 percent and 5 percent by weight, based on the weight of the monomers. A redox initiator system can b produced by including a reducing agent, such as sodium hydrosulfite, in with the free radical catalyst.

The monomers of this invention can be copolymerized with any monomers which copolymerize with acrylic monomers. However, polymers of this invention are the homopolymers of the monomers of this invention, copolymers of the monomers with monomers the homopolymers of which are soluble in water, and copolymers of the monomers of this invention and monomers which are soluble in water, 1 to 3 carbon alcohols, or water-alcohol mixtures.

Examples of monomers whose homopolymers are soluble in water are acrylamide, methacrylamide, acrylic acid, methacrylic acid, alkali metal salts of acrylic and methacrylic acid, hydroxyethyl acrylate, dimethylaminopropyl acrylamide, dimethylamino propyl methacrylamide, dimethylhydroxypropylaminopropyl methacrylamide, methacrylamidopropyl trimethyl ammonium chloride, and the like. Polymers made from these monomers and the monomers of this invention will contain from 0 up to about 70 weight percent of the copolymerizable monomers and about 30 up to 100 weight percent of the monomers of this invention.

The other comonomers which are useful in this invention are those which are soluble in water, 1 to 3 carbon alcohols, or water alcohol mixtures, but whose homopolymers are insoluble in the water, alcohol or water-alcohol mixtures. Examples of such monomers are methyl methacrylate, ethyl methacrylate, methyl acrylate, and ethyl acrylate.

Polymers made from these monomers and the monomers of this invention will contain from 0 to 30 weight percent of the copolymerizable monomers, and 70 to 100 weight percent of the monomers of this invention. Preferably, the polymers of this invention will contain up to about 20 weight percent of these copolymerizable monomers.

The homopolymers and copolymers of the monomers of this invention are soluble in water soluble alcohols or mixtures of alcohols and water. When formulated into hair grooming aids, particularly sprays for holding hair in place, the polymers dry quickly to a non-tacky state and remain non-tacky even under high humidity conditions. The polymers can be readily removed from the hair due to their somewhat detergent nature, since the pendant quaternary ammonium group is both hydrophilic and hydrophobic.

EXAMPLE 6

To a suitable reactor were added 131.1 parts of the monomer solution of Example 5 at 53.4 percent solids, 29.2 parts of the monomer solution of Example 1 at 60 percent solids, 72.2 parts of ethanol, 19.6 parts of deionized water, 0.042 part of $Na_4EDTA$ and 0.42 part of sodium persulfate. Agitation was begun and the solution was sparged with nitrogen for 30 minutes. The solution was heated to 70° C. and heating at 70° C. was continued for 4 hours. After 1 hour, the nitrogen sparge tube was raised out of the liquid to form a nitrogen sweep for the remaining three hours.

The resulting polymer solution at 35 percent solids had a viscosity of 7300 cps at 25° C. (Brookfield RV, spindle No. 4, 20 rpm). It was easily dissolved in ethanol. Films cast from the polymer dried quickly to a non-tacky state and remained non-tacky under high humidity conditions (greater than 75 percent relative humidity).

EXAMPLE 7

To a suitable reactor were added 165 parts of the monomer solution of Example 2 at 60 percent solids, 135 parts of deionized water, 0.05 part of $Na_4$ EDTA and 0.5 part of sodium persulfate. Agitation was begun and the solution was sparged with nitrogen for 30 minutes. The solution was heated to 70° C. and the nitrogen sparge tube was raised out of the liquid to from a nitrogen sweep. Heating at 70° C. was continued for 5 hours to complete the polymerization reaction.

The resulting polymer solution had a viscosity of 67,000 cps at 33 percent solids and at 25° C. (Brookfield RV spindle No. 7, 20 RPM). The polymer dissolved readily in ethanol. Films cast from the polymer solution after drying were less tacky than poly(methacrylamidopropyl trimethyl ammonium chloride).

EXAMPLE 8

Using the same procedure described in Example 6, a polymer solution was made from 29.2 parts of the monomer solution of Example 1 at 60 percent solids, 143.6 parts of methacrylamidopropyl trimethyl ammonium chloride (MAPTAC) at 50 percent solids in water, 69.2 parts of ethanol, 8 parts of deionized water, 0.042 part of $Na_4EDTA$ and 0.42 part of sodium persulfate. The resulting polymer solution had a viscosity at 25° C. of 35,500 cps at 35 percent solids (Brookfield RV, spindle No. 6, 20 RPM). The polymer dissolved only with difficulty in ethanol. Films cast from the polymer dried to a non-tacky state and remained non-tacky even in high humidity.

EXAMPLE 9

Using the same procedure described in Example 6, a polymer solution was made from 98.3 parts of the monomer solution of Example 5 at 53.4 percent solids, 61.4 parts of the monomer solution of Example 3 at 57 percent solids, 61.7 parts of ethanol, 28.6 parts of deionized water, 0.042 part of $Na_4$ EDTA and 0.42 part of sodium persulfate. The resulting polymer solution had a viscosity at 25° C. of 3700 cps at 35 percent solids (Brookfield RV spindle No. 4, 20 RPM). The polymer dissolved readily in ethanol. Films cast from the polymer solution dried quickly to a non-tacky state and remained non-tacky under high humidity conditions.

EXAMPLE 10

Using the same procedure described in Example 7, a polymer solution was formed from 240 parts of the monomer solution of Example 4 at 55 percent solids, 137.1 parts of deionized water, 0.063 part of $Na_4EDTA$ and 0.63 part of sodium persulfate. The resulting polymer solution had a viscosity at 25° C. of 7300 cps (Brookfield RV spindle No. 4, 20 RPM) and dissolved readily in ethanol. Films of the polymer dried to a state less tacky than poly MAPTAC.

EXAMPLE 11

To a suitable reactor were added 131.0 parts of the monomer solution from Example 5 at 53.4 percent solids, 8.8 parts of methyl methacrylate, 8.8 parts methacrylic acid, 74.9 parts ethanol, 26.5 parts deionized water, 0.042 parts $Na_4EDTA$, and 0.42 part sodium persulfate. Agitation was begun and the solution was sparged with nitrogen for 30 minutes. The solution was heated to 70° C. and heating at 70° C. was continued for 4 hours. After 1 hour, the nitrogen sparge tube was raised out of the liquid to form a nitrogen sweep for the remaining three hours.

The resulting polymer solution at 35 percent solids had a viscosity of 3000 cps (Brookfield RV, spindle #4, 20 RPM). It was easily dissolved in ethanol. Films cast from the polymer was less tacky then poly MAPTAC, and were much harder than previous examples. (e.g., pencil hardness of 4B as opposed to <6B for all other examples.)

EXAMPLE 12

To a suitable reactor were added 104.7 parts of the monomer solution from Example 5 at 53.4 percent solids, 23.3 parts of the monomer solution from Example 1 at 60 percent solids, 8.8 parts of methyl methacrylate, 8.8 parts of methacrylic acid, 70.3 parts of ethanol, 34.1 parts of deionized water, 0.042 part of $Na_4EDTA$, and 0.42 part of sodium persulfate. Agitation was begun and the solution was sparged with nitrogen for 30 minutes. The solution was heated to 70° C. and heating at 70° C. was continued for 4 hours. After 1 hour, the nitrogen sparge tube was raised out of the liquid to form a nitrogen sweep for the remaining three hours.

The resulting polymer solution had a viscosity of 8500 cps at 35 percent solids and at 25° C. (Brookfield RV, spindle #4, 20 RPM). The polymer dissolved readily in ethanol. Films cast from the polymer solution dried quickly to a non-tacky state and remained non-tacky under high humidity conditions. Film hardness was the same as Example 11.

The polymers made from the monomers of this invention can be reduced to viscosities below about 5 cps and solids contents below 5 weight percent with ethanol or isopropanol. These solutions can be used as hair sprays to hold the hair in place and act as an invisible hair net which holds the locks and outer strands of hair together. The polymer solutions are fast evaporating and have good adhesion to the hair without imparting stickiness or brittleness thereto. They enhance the natural sheen of the hair rather than have a dulling effect. They are easily removed from the hair by normal washing or shampooing. They are readily sprayable from aerosol-type containers without clogging the valve of the container.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A quaternary ammonium acrylic monomer having the structure

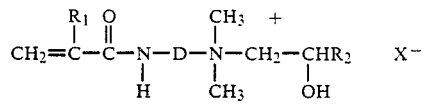

Wherein $R_1$ is H or methyl; wherein $R_2$ is an alkyl group containing 6 to 22 carbon atoms, D is an alkylene group containing 1 to 4 carbon atoms or a hydroxyalkylene group containing 2 to 4 carbon atoms, and X is an anion.

2. The monomer of claim 1 wherein $R_1$ is methyl.
3. The monomer of claim 2 wherein D is an alkylene group containing 3 carbon atoms.
4. The monomer of claim 1 wherein X is chloride.
5. The monomer of claim 1 wherein X is acetate.
6. The monomer of claim 1 wherein $R_2$ contains 6 to 14 carbon atoms.
7. The monomer of claim 1 wherein $R_1$ is methyl, D is an alkylene group containing 3 carbon atoms, $R_2$ is an alkyl group containing 6 to 14 carbon atoms and X is chloride.

* * * * *